United States Patent
Hanover

(10) Patent No.: US 6,968,223 B2
(45) Date of Patent: Nov. 22, 2005

(54) SYSTEM AND METHOD FOR WIRELESS VOICE CONTROL OF AN INTERVENTIONAL OR DIAGNOSTIC MEDICAL DEVICE

(75) Inventor: Barry Keith Hanover, Salt Lake City, UT (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 424 days.

(21) Appl. No.: 09/683,669

(22) Filed: Feb. 1, 2002

(65) Prior Publication Data

US 2003/0149342 A1 Aug. 7, 2003

(51) Int. Cl.[7] .............................................. A61B 5/05
(52) U.S. Cl. ..................... 600/407; 600/427; 600/429
(58) Field of Search ........................ 600/407, 425, 600/410, 437; 367/132–134; D24/175; 704/246

(56) References Cited

U.S. PATENT DOCUMENTS

| | | | | |
|---|---|---|---|---|
| 4,680,628 A | * | 7/1987 | Wojcik et al. ............. 378/98.2 |
| 5,303,148 A | * | 4/1994 | Mattson et al. ............. 600/437 |
| 5,335,313 A | * | 8/1994 | Douglas ..................... 704/275 |
| 5,740,801 A | * | 4/1998 | Branson ..................... 600/407 |
| 5,792,204 A | * | 8/1998 | Snell ............................ 607/32 |
| 5,807,256 A | * | 9/1998 | Taguchi et al. ............. 600/425 |
| 5,840,026 A | * | 11/1998 | Uber et al. ................. 600/431 |
| 6,083,167 A | * | 7/2000 | Fox et al. ................... 600/439 |
| 6,273,858 B1 | * | 8/2001 | Fox et al. ................... 600/466 |
| 6,416,476 B1 | * | 7/2002 | Ogasawara et al. ......... 600/443 |
| 2002/0065464 A1 | * | 5/2002 | Murphy et al. ............. 600/437 |

* cited by examiner

*Primary Examiner*—Ali Imam
(74) *Attorney, Agent, or Firm*—McAndrews, Held & Malloy, Ltd.; Peter J. Vogel; Michael A. Dellapenna

(57) ABSTRACT

A system and method of controlling a medical device through voice commands is provided that includes an input unit, such as a microphone, for receiving a voice command identifying a function associated with one of a diagnostic and interventional procedure. The system also includes a control module for directing a medical device to perform the function based on the voice command. The system includes a voice decoder that decodes the voice command into a basic signal, and a protocol translator that converts the basic signal into a signal code associated with the voice command. The control module also includes a processing unit. The control module receives the signal code and the processing unit directs the medical device to perform the function designated by the signal code.

36 Claims, 2 Drawing Sheets

SYSTEM AND METHOD FOR WIRELESS VOICE CONTROL OF AN INTERVENTIONAL OR DIAGNOSTIC MEDICAL DEVICE

BACKGROUND OF INVENTION

Certain embodiments of the present invention generally relate to improvements in the operation of an interventional or diagnostic medical device, and more particularly relate to a voice controlled medical device.

Interventional procedures typically involve interaction between a physician and a radiation technologist. Typically, the physician operates upon a patient while the radiation technologist controls an interventional medical device, such as an x-ray C-arm, that images portions of a patient during the operation. For example, during a cardiac catherization procedure, the physician typically inserts a cardiac catheter into a patient's heart through the patient's femoral artery. Typically, the physician views the progress of the cardiac catheter within the body of the patient through imaging equipment. Often, the imaging equipment is re-positioned during the procedure. The operating environment on and around the patient typically needs to remain sterile throughout the procedure. However, if the physician contacts the imaging equipment in order to control the imaging equipment during the interventional process, the sterility of the physician's hands may be threatened. That is, germs, bacteria and viruses located on the control panel of the imaging device may be transferred from the control panel, to the physician's hand. If the physician uses his/her hands during the interventional procedure, the germs, bacteria and/or viruses may be transferred to the body of the patient. Therefore, in order to maintain the sterile environment, the physician typically must sterilize his/her hands after the he/she contacts the controls of the imaging device.

Often, however, the imaging equipment and controls within a cardiac catherization lab are sterile. Typically, the physician controls the system. The imaging equipment may include controls that are not on control panel. Rather, some controls may be located remote from the control panel. In an effort to avoid complicating the control panel, some controls are not included within the control panel. Because the control panels may not include all the controls for the control panel, the physician may have to interrupt an operating procedure to activate certain functions of the system. Additionally, operating the control panel requires manual manipulation of the controls. Thus, a physician typically operates with the imaging equipment with at least one hand. The physician's hand(s), however, typically are better used in the actual operating environment on or within the patient.

In an effort to use both hands within the operating environment, the physician often directs the radiation technologist, or other assistant to control the imaging device. Typically, the physician verbally directs the radiation technologist to control positioning and imaging characteristics of the imaging device. The physician, however, may not have direct control of the imaging device. Instead, the physician typically directs a "middle man" such as the radiation technologist to control the imaging device to ensure that the sterility of the operating environment is maintained.

As diagnostic and interventional procedures become more complex, indirect control of imaging devices poses certain drawbacks. Indirect control of imaging devices may cause confusion and control inaccuracies. That is, the assistant controlling the imaging device may misinterpret the physician's directions. Also, additional time is required for the assistant to control the imaging device as per the physician's instructions. For example, the assistant may move the imaging device too fast or slow for the physician; or the assistant may image an anatomical structure from an undesired angle. If the assistant misinterprets the physician's directions, or the physician's directions are unclear, additional time for the procedure is required to eliminate confusion and correct any mistakes. Further, mistakes in the positioning and imaging of the imaging device may cause mistakes in diagnosis and treatment of the patient.

In order to provide direct control of a medical device by the physician, some medical systems include foot controls. Operation of a medical system through a foot control typically ensures that the operating environment within the patient remains sterile and the physician's hands remain available for patient treatment. However, foot controls typically are cumbersome because other functions of the medical system may be controlled through a foot control. For example, many x-ray systems include a foot control for initiating x-ray imaging. Adding additional controls on a foot control console may be confusing due to the fact that the physician may have to repeatedly look down at the foot control to make sure that he/she is activating the correct control. Additionally, foot controls may not be practicable with surgical applications wherein the physician is standing.

Thus, a need has existed for more direct control of medical systems, such as interventional fluoroscopic imaging systems. Additionally, a need has existed for a safer and more efficient system and method for controlling an interventional medical device.

SUMMARY OF INVENTION

In accordance with an embodiment of the present invention, a voice controlled medical system has been developed that includes an input unit, such as a microphone, for receiving a voice command identifying a function associated with a diagnostic and/or interventional procedure. The system also includes a control module for directing a medical device included within the system to perform the function based on the voice command.

An embodiment of the present invention includes a voice decoder for decoding the voice command into a basic signal. A protocol translator converts the basic signal into a signal code representing the function identified by the voice command, and a processing unit directs the medical device to perform the function designated by the signal code.

In another embodiment of the present invention a voice decoder is used with a magnetic resonance imaging (MRI) device. In yet another embodiment of the present invention a voice decoder is used with a computerized tomography imaging device or a fluoroscopic imaging device, such as an x-ray C-arm.

Another embodiment of the present invention includes a transmitter associated with the input device. The transmitter transmits the signal code to a receiver provided at the medical device. The receiver receives the signal code. The medical device and the input device may be remotely located from one another. The signal code may be transmitted to the receiver through infrared (IR) or radio frequency (RF) signals.

The system may also include a remote control. The remote control may include a remote control receiver for receiving the signal code transmitted from the transmitter. The remote control transfers the signal code to the receiver provided at the medical device.

In another embodiment of the present invention, a method is provided for controlling a medical device through voice commands. The method includes the steps of speaking a voice command into an input device, such as a microphone. The method also includes the step of decoding the voice command into a basic code and converting the basic code into a signal code representing the function identified by the voice command. The method also includes the step of transmitting the signal code to a receiver of a medical unit including the medical device, and directing the medical device to perform the function designated by the signal code. Transmission of the signal code may be wirelessly executed.

In another embodiment of the present invention, voice control may be used in conjunction with a simple foot or hand switch that is activated in order for a voice command to be effected. The activating foot or hand switch provides a safety check, which is useful when controlling motion or x-ray exposure operations.

BRIEF DESCRIPTION OF DRAWINGS

The foregoing summary, as well as the following detailed description of the preferred embodiments of the present invention, will be better understood when read in conjunction with the appended drawings. For the purpose of illustrating the invention, there is shown in the drawings, embodiments which are present preferred. It should be understood, however, that the present invention is not limited to the precise arrangements and instrumentality shown in the attached drawings.

DETAILED DESCRIPTION

Figure 1:
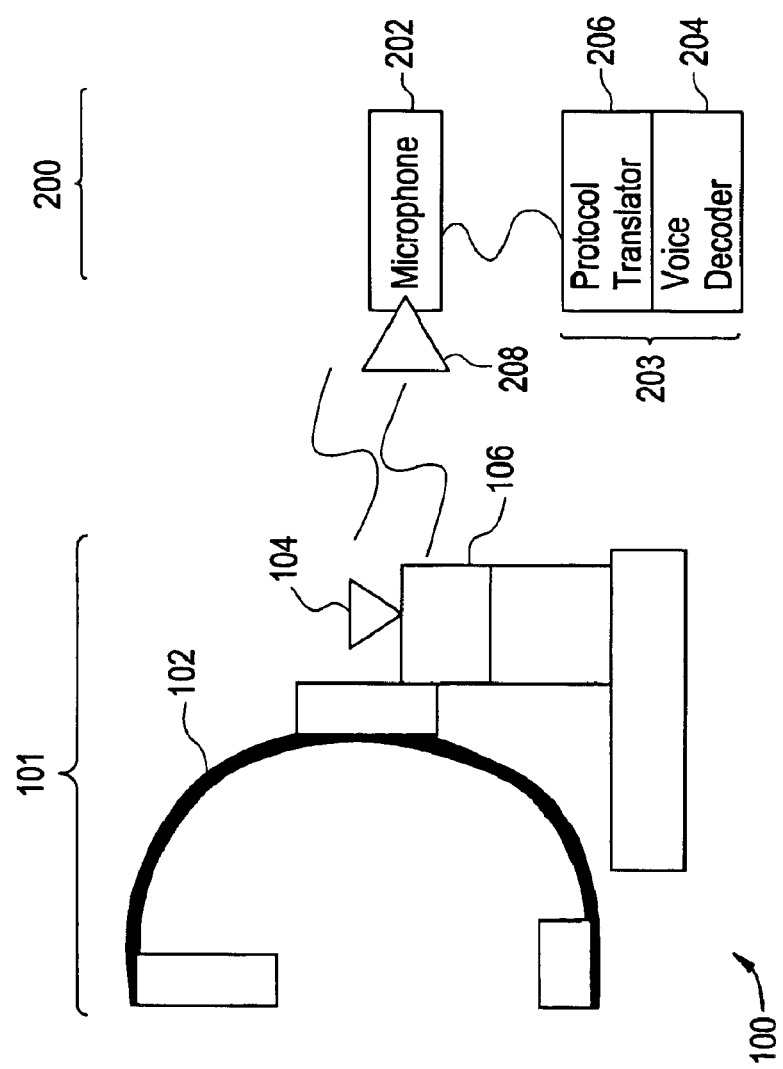
FIG. 1 illustrates a voice controlled medical system according to an embodiment of the present invention.

FIG. 1 illustrates a voice controlled medical system 100 according to an embodiment of the present invention. The voice controlled medical system 100 includes a medical unit 101 and a voice command unit 200. The medical unit 101 includes a medical device, or apparatus 102, a receiver 104 and a processing unit 106. The voice command unit 200 includes a transmitter 208, an electronics package 203, an input unit, such as a microphone 202 and a power supply, such as batteries (not shown). The electronics package 203 includes a voice decoder 204 and a protocol translator 206. Alternatively, a remote control (not shown) may be included within the system.

The medical unit 102 may be a fluoroscopic imaging device, such as an x-ray C-arm. Optionally, the medical unit 102 may be a computerized tomography (CT) device, a magnetic resonance imaging (MRI) device, or another interventional or diagnostic medical device. The medical device 102 is controlled and operated through the processing unit 106. The processing unit 106 is connected to the medical device 102 through wiring (not shown). The processing unit 106 is further connected to the receiver 104 through wiring (not shown). Preferably, the processing unit 106 is contained within a housing. The processing unit 106 may be directly attached to the medical device 102, or may be discrete from the medical device 102. For example, the processing unit 106 may be contained within a housing attached to the medical device 102 or may be contained within a portable cabinet that is remote from the medical device 102.

The voice command unit 200 is remote from the medical unit 101. Preferably, the voice command unit 200 communicates with the medical unit 100 through wireless signals, such as infrared (IR) or radio frequency (RF) signals. Alternatively, the voice command unit 200 may be connected to the medical unit 100 through wires. The electronics package 203 is connected to the microphone 202 through wires 207. Preferably, the electronics package 203 is enclosed within a single housing and worn on a belt of the operator. For example, the microphone 202 may be sewn in, or otherwise worn on a lapel, or attached to a surgical mask/glasses of the operator; whereas the electronics package 203 is worn on the belt of the operator. Alternatively, the electronics package 203 may be directly attached to the microphone 202. Also, alternatively, the microphone 202, transmitter 208 and the electronics package 203 may be included within a head unit (not shown).

In operation, an operator, or physician speaks a voice command into the microphone 202. The voice command identifies a function associated with a medical diagnostic and/or interventional procedure. For example, the voice command may be associated with a movement or imaging function of the medical device 102. The voice command travels to the electronics package 203. The voice decoder 204 of the electronics package 203 decodes the voice command into a basic signal. The protocol translator 206 then receives the basic signal and converts the basic signal into a signal code that the processing unit 106 of the medical unit 101 recognizes. That is, the protocol translator 206 includes a library of functions. Each function is associated with a basic signal, which is in turn associated with an electronic signature of a voice command. The processing unit 106 recognizes the signal code, interprets the signal code, and directs the medical device 102 to perform a function designated by the signal code. Thus, the processing unit 106 directs the medical device 102 to perform a function based on the voice command.

For example, if the processing unit recognizes a first signal code as a command to move the medical device 102 in a particular fashion, the protocol translator 206 converts a corresponding basic signal, associated with a voice command to move the medical device 102, to the recognized signal code. The protocol translator 206 then sends the signal code to the transmitter 208. The transmitter 208 then transmits the signal code to the receiver 104 of the medical unit 101. If the transmitter 208 transmits the signal code through an IR signal, the transmitter 208 typically is within the line of sight of the receiver 104. Alternatively, the system may include reflecting surfaces that reflect the IR signal within a room that the system 100 is contained. The reflecting surfaces may allow the transmitter 208 to be positioned out of the line of sight of the receiver 104. That is, the reflecting surfaces may assist in re-directing the IR signal from the transmitter 208 to the receiver 104. Once the receiver 104 receives the signal code, the signal code is sent to the processing unit 106. The processing unit 106 then directs the medical device 102 to perform a function based on the recognized signal code.

For example, if the medical device 102 is a C-arm, and the physician desires to rotate the C-arm in a counter clockwise direction, the physician speaks, into the microphone 202, a voice command associated with counter clockwise rotation. For example, the physician may state, "Rotate counter clockwise, ninety degrees." The voice decoder 204 then decodes the voice command into a basic code associated with 90 degree counter clockwise rotation. The protocol translator 206 then receives the basic code. The protocol translator 206 searches the library included within the protocol translator for an associated signal code. If the protocol translator 206 does not find an associated signal code, the protocol translator does not send a signal code to the transmitter 208. If, however, the protocol translator 206 recognizes the basic code and finds an associated signal code within the library, the protocol translator 206 converts the basic code into the associated signal code. The protocol translator 206 then sends the signal code to the transmitter 208. The transmitter 208 transmits the signal code to the receiver 104 of the medical unit 100 by way of IR or RF signals. The processing unit 106 receives the signal code from the receiver 104. The processing unit 106 directs the medical device 102, such as a C-arm, to rotate ninety degrees counter clockwise. Alternatively, the signal code may be transmitted from the transmitter 208 to a remote receiver (not shown) included within the remote control or a repeater included within the system 100. The remote control or repeater may then transmit the signal code to the receiver 104 of the medical unit 101.

Various functions of the medical device may be controlled through voice control. Functions such as positioning, movement, and imaging capabilities of the medical device 102 may be controlled through voice operation. For example, the physician may control the rotation of the medical device 102, such as a C-arm, the time and intensity of imaging, viewing of an image on a video display and various other features of the medical device 102 and medical unit 100. The functions that may be controlled through a control panel (not shown) or a remote control of the imaging unit 101 may be controlled through voice control. Because the functions and parameters of the medical unit 101 may be controlled through voice control, the operator of the medical unit 101 may perform diagnostic and/or interventional procedures on a patient while simultaneously operating the medical device 102. The physician may continue to operate on the patient without continuously removing his/her hands from the interventional tools. Thus, interventional operations are safer, quicker, and more efficient as compared to non-voice controlled systems.

Alternatively, the processing unit 106 of the medical unit 101 may include one or both of the voice decoder 204 and the protocol translator 206; in which case, the transmitter 208 transmits the basic code or the signal code to the receiver 104. Optionally, the receiver 104 may include an input device and directly receive voice commands from a physician. The voice decoder 204 and the protocol translator 206 may be contained within the processing unit 106 instead of being remotely located from the medical unit 101.

Figure 2:
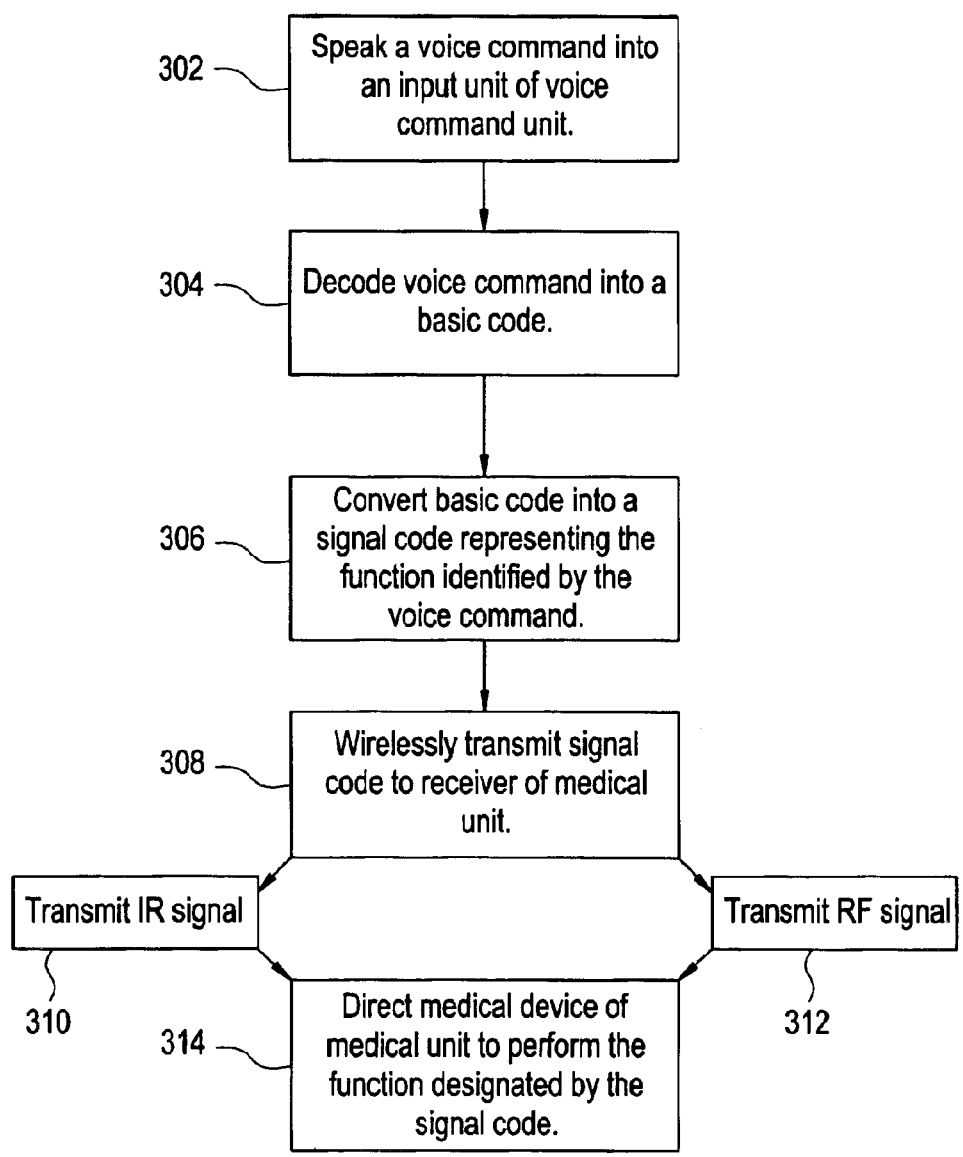
FIG. 2 is a flow chart of a method of controlling a medical device through voice commands.

FIG. 2 illustrates a flow chart 300 of a method of controlling a medical device through voice commands in accordance with an embodiment of the present invention. At step 302, a physician, or operator, speaks a voice command into the input device, such as the microphone 202, of the voice command unit 200. The voice command is decoded into a basic code by the voice decoder 204 at step 304. The basic code is then converted to a recognizable signal code by the protocol translator 206 at step 306. The signal code represents the function identified by the voice command. At step 308, the signal code is wirelessly transmitted to the receiver 104 of the medical unit 101. At step 310, the signal code is transmitted by way of an IR signal. Alternatively, at step 312, the signal code may be transmitted through an RF signal. The signal code is then sent to the processing unit 106. At step 314, the processing unit 106 directs the medical device 102 of the medical unit 101 to perform the function designated by the signal code. Therefore, the processing unit 106 directs the medical device 102 to perform the function based on the voice command.

Thus, embodiments of the present invention provide more direct control of medical systems, such as interventional or diagnostic fluoroscopic imaging systems. Additionally, embodiments of the present invention provide a safer and more efficient system and method for controlling an interventional medical device.

While particular elements, embodiments and applications of the present invention have been shown and described, it will be understood, of course, that the invention is not limited thereto since modifications may be made by those skilled in the art, particularly in light of the foregoing teachings. It is therefore contemplated by the appended claims to cover such modifications that incorporate those features coming within the scope of the invention.

What is claimed is:

1. A system for controlling a medical device through voice commands, comprising:
   a medical device for performing at least one of interventional and diagnostic procedures;
   an input unit for receiving a voice command identifying a function associated with one of a diagnostic and interventional procedure, wherein the function includes movement of said medical device; and
   a control module for directing said medical device to perform the function based on said voice command.

2. The system of claim 1 wherein said input unit is a microphone.

3. The system of claim 1 further including a voice decoder for decoding said voice command into a basic signal.

4. The system of claim 3 further including a protocol translator for converting said basic signal into a signal code representing the function identified by said voice command.

5. The system of claim 4 wherein said control module includes a processing unit for directing said medical device to perform said function designated by said signal code.

6. The system of claim 4 further including a transmitter for transmitting said signal code to said control module.

7. The system of claim 1 wherein said medical device is an interventional medical device.

8. The system of claim 1, further comprising additional functions including positioning and imaging characteristics of said medical device, wherein said control module is configured to direct said medical device to perform the function and the additional functions based on said voice command and additional voice commands, respectively.

9. A system for controlling a medical device through voice commands, comprising:
   a medical device for performing one of a medical diagnostic and interventional procedure;
   a microphone for receiving a voice command identifying a function associated with one of said medical diagnostic and interventional procedure, wherein the function includes movement of said medical device;
   a voice decoder for decoding said voice command into a basic signal; and
   a protocol translator for converting said basic signal into a signal code representing said function identified by said voice command; and
   a processing unit for directing said medical device to perform said function designated by said signal code.

10. The system of claim 9 wherein said medical device is an interventional medical device.

11. The system of claim 9 wherein said signal code is an infrared (IR) signal code.

12. The system of claim 9 wherein said signal code is a radio frequency (RF) signal code.

13. The system of claim 9 wherein said medical device is a magnetic resonance imaging (MRI) device.

14. The system of claim 9 wherein said medical device is a computerized tomography imaging device.

15. The system of claim 9 wherein said medical device is a fluoroscopic imaging device.

16. The system of claim 9 further including:
a transmitter associated with said microphone, wherein said transmitter transmits said signal code, and
a receiver provided at said medical device for receiving signal code, wherein said medical device and said microphone are remotely located from one another.

17. The system of claim 16 further including a remote control, wherein said remote control includes a remote control receiver for receiving said signal code transmitted from said transmitter, and wherein said remote control transfers said signal code to said receiver provided at said medical device.

18. The system of claim 9, further comprising additional functions including positioning and imaging characteristics of said medical device, wherein said control module is configured to direct said medical device to perform said function and said additional functions based on said voice command and additional voice commands, respectively.

19. A method of controlling a medical device through voice commands, comprising:
speaking a voice command into a microphone, said voice command identifying a function associated with one of a diagnostic and interventional procedure, wherein said function includes movement of the medical device;
decoding said voice command into a basic code;
converting said basic code into a signal code representing the function identified by said voice command;
transmitting said signal code to a receiver of a medical unit including the medical device; and
directing said medical device to perform said function designated by said signal code.

20. The method of claim 19 wherein said transmitting step includes wirelessly transmitting said signal code to the receiver of the medical unit.

21. The method of claim 19 wherein said transmitting step includes transmitting said signal code through infrared signals to the receiver of the medical unit.

22. The method of claim 19 wherein said transmitting step includes transmitting said signal code through radio frequency signals to the receiver of the medical unit.

23. The method of claim 19, further comprising speaking additional voice commands into the microphone, wherein said additional voice commands identify additional functions including positioning and imaging characteristics of the medical device; and directing said medical device to perform said additional functions.

24. A system for operating an interventional fluoroscopic imaging apparatus through voice commands, comprising:
an interventional fluoroscopic imaging device for performing one of a medical diagnostic and interventional procedure;
an input unit for receiving a voice command identifying a function associated with one of a diagnostic and interventional procedure, wherein the function includes movement of the said interventional fluoroscopic imaging device;
a voice decoder for decoding said voice command into a basic signal;
a protocol translator for converting said basic signal into a signal code representing said function identified by said voice command; and
a processing unit for directing said interventional fluoroscopic imaging apparatus to perform said function designated by said signal code.

25. The system of claim 24 wherein said input unit is a microphone.

26. The system of claim 24 further including:
a transmitter associated with said microphone, wherein said transmitter wirelessly transmits said signal code, and
a receiver provided at said medical device for receiving said signal code, wherein said medical device and said microphone are remotely located from one another.

27. The system of claim 24 wherein said signal code is an infrared (IR) signal code.

28. The system of claim 24 wherein said signal code is a radio frequency (RF) signal code.

29. A method of controlling an interventional fluoroscopic imaging device through voice commands, comprising:
speaking a voice command into an input unit, said voice command identifying a function associated with one of a diagnostic and interventional procedure, wherein the function includes movement of the interventional fluoroscopic imaging device;
decoding said voice command into a basic code;
converting said basic code into a signal code representing the function identified by said voice command;
transmitting said signal code to a receiver of a medical unit including the interventional fluoroscopic imaging device; and
directing the interventional fluoroscopic imaging device to perform said function designated by said signal code.

30. The method of claim 29 wherein said transmitting step includes wirelessly transmitting said signal code to the receiver of the medical unit.

31. The method of claim 29 wherein said transmitting step includes transmitting said signal code through infrared signals to the receiver of the medical unit.

32. The method of claim 29 wherein said transmitting step includes transmitting said signal code through radio frequency signals to the receiver of the medical unit.

33. A system for operating an interventional medical device through voice commands, comprising:
an interventional medical device for performing one of a medical diagnostic and interventional procedure; and
a processing unit for directing said medical device to perform functions based on voice commands, wherein the functions include movement, positioning and imaging capabilities of said interventional medical device, said processing unit including:
a voice decoder for decoding said voice commands into basic signals; and
a protocol translator for converting said basic signals into signal codes representing said functions identified by said voice commands, said processing unit directing said medical device to perform functions designated by said codes.

34. The system of claim 33 wherein said interventional medical device is a magnetic resonance imaging (MRI) device.

35. The system of claim 33 wherein said interventional medical device is a computerized tomography imaging device.

36. The system of claim 33 wherein said interventional medical device is a fluoroscopic imaging device.

* * * * *